US00PP08439P

United States Patent [19]

Zaiger et al.

[11] Patent Number: Plant 8,439

[45] Date of Patent: Oct. 26, 1993

[54] PEACH TREE "SCARLET SNOW"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95358

[21] Appl. No.: 2,016

[22] Filed: Jan. 8, 1993

[51] Int. Cl.[5] ..... A01H 5/00

[52] U.S. Cl. ..... Plt./42.1

[58] Field of Search ..... Plt./42.1

*Primary Examiner*—James R. Feyrer

[57] ABSTRACT

A new and distinct variety of peach tree with the following combination of unique features that are desirable in a new variety.

1. Heavy and regular production of fruit.
2. Production of very firm, white flesh fruit with good handling and shipping quality.
3. Fruit that will stay firm on the three 7 to 10 days after maturity (shipping ripe).
4. Fruit with excellent flavor and eating quality.
5. Late maturity of white flesh fruit.
6. Fruit with an attractive red skin blush.
7. Vigorous upright growth.

1 Drawing Sheet

ORIGIN OF THE VARIETY

The new and distinct variety of peach tree was originated by us in our experimental orchard located near Modesto, Calif. as a first generation cross between two selected seedlings with the identification numbers 38EB272 and 52EB425. The female parent 38EB272 originated from a cross between two selected seedlings, one an open pollinated seedling from Golden Supreme Peach (unpatented) seed and the other from a cross between O'Henry Peach (U.S. Plant Pat. No. 2,964) and Giant Babcock Peach (U.S. Plant Pat. No. 1,353). The pollen parent 52EB425 originated from a cross between two selected seedlings, one seedling originated from a nectarine of unknown parentage and the other from a nectarine which originated from open pollinated Golden Supreme Peach (unpatented). A large group of these first generation seedlings were grown and maintained under close observation by us, during which time we recognized the desirable fruit characteristics described above and the present variety was selected for asexual reproduction and commercialization.

ASEXUAL REPRODUCTION OF THE VARIETY

Asexual reproduction of the new and distinct variety was performed by budding in our experimental orchard located near Modesto, Calif. and shows that all characteristics run true to the original tree and are established and transmitted through succeeding propagations.

SUMMARY OF THE VARIETY

The present new and distinct variety of peach tree is of large size, vigorous upright growth and a regular and productive bearer of large, white flesh, freestone fruit with a mild, subacid, sweet flavor with excellent eating quality. The fruit is further characterized by having very firm flesh, the ability to hang on the tree 7 to 10 days after maturity (shipping ripe), having good handling and shipping quality, a white skin ground color overspread with an attractive red blush and ripening in the late maturity season, approximately 35 days after O'Henry Peach (U.S. Plant Pat. No. 2,964).

DESCRIPTION OF THE PHOTOGRAPHS

The accompanying photographs show typical specimens of the foliage and fruit of the new and distinct peach variety. The illustrations show the upper and lower surface of the leaves, an exterior and a fruit divided in its suture plane to reveal flesh coloration, pit cavity, and a stone remaining in place. The photographic illustrations were taken shortly after being picked (firm ripe) and the colors are as nearly true as is reasonably possible in a color representation of this type.

DESCRIPTION OF THE VARIETY

The following is a detailed botanical description of the new and distinct variety of peach tree, its flowers, fruit and foliage as based on observations of the specimen grown in our experimental orchard located near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright. Usually pruned to vase shape.
- *Production.*—Productive.
- *Bearing.*—Regular.
- *Density.*—Medium dense.

Trunk:
- *Size.*—Medium to stocky.
- *Texture.*—Medium shaggy.
- *Color.*—Grayish brown to brown (5-E-4) to (6-E-5).

Branches:
- *Size.*—Medium.
- *Texture.*—Varies from smooth to medium rough with maturity.
- *Lenticels.*—Medium size. Medium number.
- *Color.*—Light brown to brown.

Leaves:
- *Size.*—Medium to large. Average length — 6¼"to 6¾". Average width — 1½" to 1⅝".
- *Form.*—Lanceolate-pointed.

*Texture.*—Smooth.
*Thickness.*—Medium.
*Margin.*—Crenate.
*Petiole.*—Medium length. Medium thickness.
*Glands.*—Reniform. Number varies from 0 to 5. Average number 2. Located on base of leaf blade and upper portion of petiole.
*Color.*—Upper surface green to dark green (26-F-5) to (25-F-8). Lower surface dull green to grayish green (26-E-5) to (26-D-5).

Flower buds:
*Size.*—Small to medium.
*Form.*—Plump.
*Length.*—Medium.
*Pubescence.*—Pubescent.

Flowers:
*Size.*—Medium — non-showy.
*Blooming period.*—Mar. 3, 1992 to Mar. 9, 1992. Varies slightly due to climatic conditions.
*Color.*—Pink.
*Pollen.*—Present.

Fruit:
*Maturity when described.*—Firm ripe.
*Date of first picking.*—Aug. 24, 1992.
*Date of last picking.*—Sep. 2, 1992.
*Size.*—Large. Average diameter axially 3" to 3¼". Average transversely in suture plane 3" to 3¼".
*Form.*—Globose — slightly flattened on stem end.
*Suture.*—Shallow but pronounced, extends from base to apex.
*Ventral surface.*—Nearly rounded, very slightly lipped.
*Apex.*—Varies from rounded to slight pistil point.
*Base.*—Retuse.
*Cavity.*—Rounded to slightly elongated in suture plane. Average depth — ½". Average breadth — ¾".

Skin:
*Thickness.*—Medium.
*Texture.*—Medium, tenacious to flesh.
*Tendency to crack.*—None.
*Down.*—Moderate amount, short to very short in length.
*Color.*—Ground color white to pinkish white (8-A-1) to (8-A-2). Overspread with light red to geranium red blush (11-A-5) to (11-B-7).

Flesh:
*Texture.*—Very firm.

*Ripens.*—Evenly.
*Fibers.*—Small, tender.
*Juice.*—Moderate.
*Flavor.*—Excellent, subacid, mild, sweet.
*Aroma.*—Moderate.
*Eating quality.*—Excellent.
*Amygdalin.*—Undetected.
*Color.*—White to pinkish white (7-A-1) to (7-A-2). Pit cavity red to madder red (12-A-7) to (12-B-8). Color extends from pit cavity outward into flesh, heavier near apex.

Stone:
*Type.*—Freestone.
*Size.*—Large. Average length 1½". Average width 1⅛". Average thickness ⅝".
Form.—Ovoid.
*Base.*—Mostly straight — some rounded.
*Apex.*—Acuminate.
*Sides.*—Equal to unequal.
*Surface.*—Irregularly furrowed toward apex, ridges usually rounded, pitted toward base.
*Tendency to split.*—None.
*Color.*—Brown to reddish brown (8-E-6) to (9-E-6).

Use: Dessert.
*Market.*—Local and long distance.
Keeping quality: Good.
Shipping quality: Good.

The new and distinct variety of peach tree, its flowers, foliage and fruit described above may vary in slight detail due to variations in climate, soil conditions and cultural practices under which the variety may be grown. The botanical description above is that of the variety grown under the ecological conditions prevailing near Modesto, Calif.

We claim:

1. A new and distinct variety of peach tree, substantially as illustrated and described, characterized by its large size, vigorous, upright growth and being a regular and productive bearer of large, late maturing, white flesh, freestone fruit with excellent flavor and eating quality; the fruit is further characterized by having very firm flesh, good handling and shipping quality and having a white skin ground color overspread with an attractive red blush.

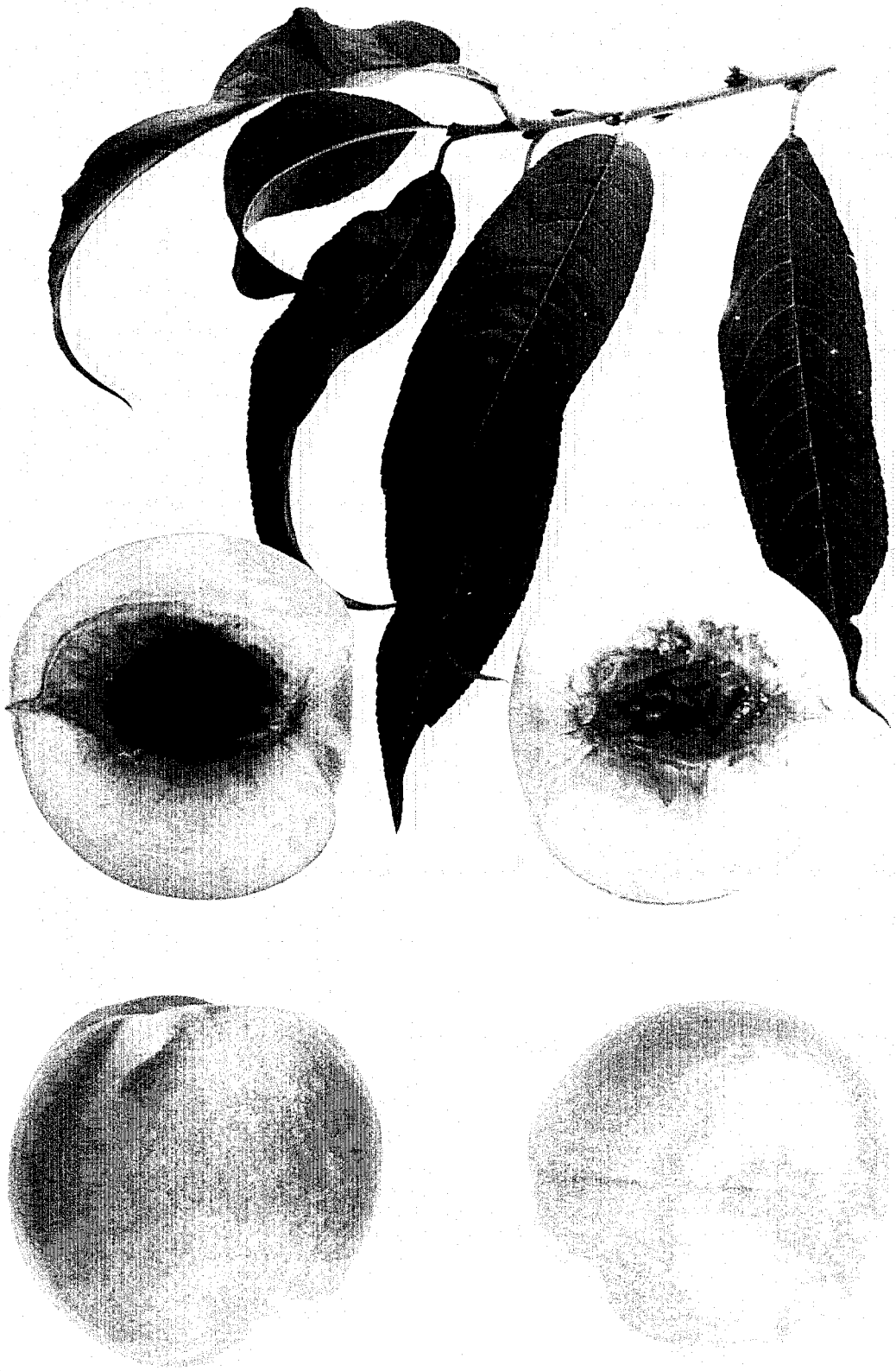

* * * * *